US012578529B2

(12) United States Patent
Lee et al.

(10) Patent No.: US 12,578,529 B2
(45) Date of Patent: Mar. 17, 2026

(54) OPTICAL TRANSMITTER

(71) Applicant: ROCKLEY PHOTONICS LIMITED, Altrincham (GB)

(72) Inventors: Yi Ho Lee, Breinigsville, PA (US); Jeffrey Driscoll, San Jose, CA (US); James Dongyoon Oh, Alhambra, CA (US)

(73) Assignee: Rockley Photonics Limited, Altrincham (GB)

( * ) Notice: Subject to any disclaimer, the term of this patent is extended or adjusted under 35 U.S.C. 154(b) by 677 days.

(21) Appl. No.: 18/060,813

(22) Filed: Dec. 1, 2022

(65) Prior Publication Data

US 2023/0384514 A1     Nov. 30, 2023

Related U.S. Application Data

(60) Provisional application No. 63/346,300, filed on May 26, 2022.

(51) Int. Cl.
| | |
|---|---|
| *G02B 6/12* | (2006.01) |
| *G01J 9/02* | (2006.01) |
| *A61B 5/1455* | (2006.01) |
| *G02B 6/293* | (2006.01) |

(52) U.S. Cl.
CPC ........ *G02B 6/12019* (2013.01); *G01J 9/0246* (2013.01); *G02B 6/12033* (2013.01); *A61B 5/1455* (2013.01); *G01J 2009/023* (2013.01); *G01J 2009/0288* (2013.01); *G02B 2006/12104* (2013.01); *G02B 2006/12121* (2013.01); *G02B 2006/12164* (2013.01); *G02B 6/29301* (2013.01)

(58) Field of Classification Search
None
See application file for complete search history.

(56) References Cited

U.S. PATENT DOCUMENTS

| | | | | |
|---|---|---|---|---|
| 2004/0067006 A1* | 4/2004 | Welch | ................ | G02B 6/12011 |
| | | | | 385/14 |
| 2005/0249509 A1* | 11/2005 | Nagarajan | ................. | H01S 5/12 |
| | | | | 398/198 |
| 2009/0279828 A1* | 11/2009 | Nilsson | .............. | G02B 6/12033 |
| | | | | 372/32 |
| 2022/0107229 A1* | 4/2022 | Barnard | ................. | G01K 11/00 |

OTHER PUBLICATIONS

Halir, R. et al., "Direct and Sensitive Phase Readout for Integrated Waveguide Sensors", IEEE Photonics Journal, Aug. 6, 2013, 7 pages, vol. 5, No. 4, IEEE.
Milvich, J. et al., "Mach-Zehnder Interferometer Readout for Instantaneous Sensor Calibration and Extraction of Endlessly Unwrapped Phase", 2017, pp. 567-568, IEEE.

* cited by examiner

*Primary Examiner* — Chad H Smith
(74) *Attorney, Agent, or Firm* — Womble Bond Dickinson (US) LLP

(57) ABSTRACT

A system including an optical transmitter. In some embodiments, the system includes: a first array of lasers; a first wavelength multiplexer, connected to the first array of lasers; a first coupler, connected to the wavelength multiplexer; and a first wavelength meter, connected to a first output of the first coupler.

17 Claims, 10 Drawing Sheets

OPTICAL TRANSMITTER

CROSS-REFERENCE TO RELATED APPLICATION(S)

The present application claims priority to and the benefit of U.S. Provisional Application No. 63/346,300, filed May 26, 2022, entitled "SYSTEM FOR SPECTROMETRY OR SPECTROPHOTOMETRY", the entire content of which is incorporated herein by reference.

FIELD

One or more aspects of embodiments according to the present disclosure relate to spectrometry, and more particularly to a photonic integrated circuit for use as a transmitter in a spectrophotometer.

BACKGROUND

For a variety of health assessment and health care applications, it may be advantageous to have information regarding the chemical composition of tissues of a subject. For example, the chemical composition of the blood of a subject may provide information about the subject's hydration level, kidney function, and the like.

It is with respect to this general technical environment that aspects of the present disclosure are related.

SUMMARY

According to an embodiment of the present disclosure, there is provided a system, including: a first array of lasers; a first wavelength multiplexer, connected to the first array of lasers; a first coupler, connected to the wavelength multiplexer; and a first wavelength meter, connected to a first output of the first coupler.

In some embodiments, the first coupler is configured to deliver at least 70% of the optical power received at the first input of the first coupler to a first output of the first coupler.

In some embodiments, the first coupler further has: a first input; and a second input connected to a test input facet.

In some embodiments, the system further includes a first splitter having an input, a first output and a second output, wherein a first output of the first coupler is connected to the input of the first splitter, wherein: the first output of the first splitter is connected through a first optical path to a free propagation region, the second output of the first splitter is connected through a second optical path to the free propagation region.

In some embodiments, the length of the second optical path is at least 10% greater than the length of the first optical path.

In some embodiments: the first optical path and the second optical path are part of a passive optical phased array configured to steer an output beam through an angle corresponding to a wavelength change; and the wavelength change is less than a longitudinal mode spacing of a laser of the first array of lasers.

In some embodiments, the second optical path includes a spiral waveguide.

In some embodiments, the first optical path includes a multimode waveguide and the second optical path includes a multimode waveguide.

In some embodiments, the first optical path includes a heater.

In some embodiments, the system includes an optical phased array including the first optical path and the second optical path, and further including a deformable reflector, the optical phased array being configured to steer a free-space beam across the deformable reflector.

In some embodiments, the system further includes: a first cascade of one or more spiral waveguides connected to the second output of the first splitter; a second splitter having an input, a first output, and a second output, the input of the second splitter being connected to the first output of the first splitter; a third splitter having an input, a first output, and a second output, the input of the third splitter being connected to the first cascade of one or more spiral waveguides; a second cascade of one or more spiral waveguides connected to the second output of the second splitter; and a third cascade of one or more spiral waveguides connected to the second output of the third splitter.

In some embodiments, the first array of lasers includes 50 lasers.

In some embodiments, the wavelength separation of two lasers of the first array of lasers is between 3 nm and 15 nm.

In some embodiments, the system further includes a temperature sensor configured to measure the temperature of the first wavelength meter.

In some embodiments, the temperature sensor is a diode temperature detector.

In some embodiments, the system further includes a photodiode configured to receive a portion of the light at a second output of the first coupler and to measure the output power of a currently operating laser.

In some embodiments, the system further includes: a second array of lasers; a second wavelength multiplexer; and a second wavelength meter, the second wavelength multiplexer having: a plurality of inputs each connected to a respective one of the lasers of the second array of lasers, and an output, the output of the second wavelength multiplexer being connected to the second wavelength meter.

In some embodiments: the first wavelength meter is a Mach Zehnder interferometer wavelength meter, and the second wavelength meter is a Mach Zehnder interferometer wavelength meter.

In some embodiments: the frequencies of the lasers of the first array of lasers are uniformly spaced to within 20%, the frequencies of the lasers of the second array of lasers are uniformly spaced to within 20%, the average frequency separation of the lasers of the first array of lasers is greater than the average frequency separation of the lasers of the second array of lasers by at least 30%, N/2 times the free spectral range of the first wavelength meter is within 10% of the average frequency separation of the lasers of the first array of lasers, M/2 times the free spectral range of the second wavelength meter is within 10% of the average frequency separation of the lasers of the second array of lasers, and N and M are integers.

In some embodiments, the first wavelength multiplexer, the first coupler, and the first wavelength meter are integrated onto a silicon photonic integrated circuit.

BRIEF DESCRIPTION OF THE DRAWINGS

These and other features and advantages of the present disclosure will be appreciated and understood with reference to the specification, claims, and appended drawings wherein:

DETAILED DESCRIPTION

Figure 1A:
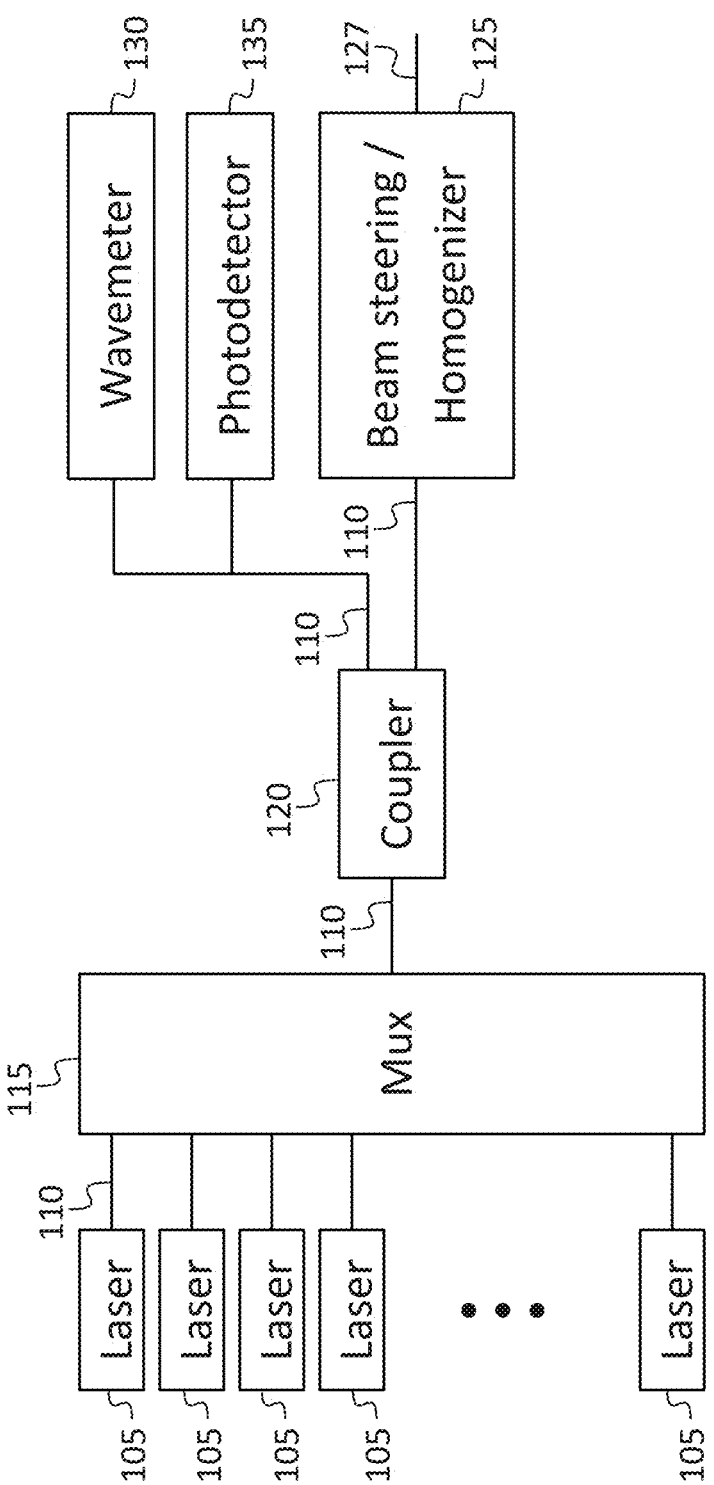
FIG. 1A is a block diagram of a photonic integrated circuit, according to an embodiment of the present disclosure.

The detailed description set forth below in connection with the appended drawings is intended as a description of exemplary embodiments of an optical transmitter provided in accordance with the present disclosure and is not intended to represent the only forms in which the present disclosure may be constructed or utilized. The description sets forth the features of the present disclosure in connection with the illustrated embodiments. It is to be understood, however, that the same or equivalent functions and structures may be accomplished by different embodiments that are also intended to be encompassed within the scope of the disclosure. As denoted elsewhere herein, like element numbers are intended to indicate like elements or features.

Spectroscopic (e.g., spectrophotometric) sensing may provide useful information related to the health state of a patient, or "subject", such as the hydration level of the subject, or glucose levels in the tissue (e.g., in the blood) of the subject. A spectrophotometer may include a transmitter capable of transmitting light at various wavelengths, and a receiver for measuring a return signal. The transmitter may illuminate the skin of the subject; some of the light may then propagate, along various paths extending (i) within or below the skin of the subject, and (ii) back out of the subject, forming the return signal, which may be detected by a photodetector (e.g., a photodiode). The intensity of the return signal may depend on the extent to which the wavelength transmitted into the subject is absorbed within the subject, which in turn may depend on the chemical composition of the tissues through which the light propagates. As such, the ratio of the intensity of the return signal to the intensity of the light transmitted by the transmitter may be used to infer aspects of such chemical compositions.

A SWIR (short wavelength infra-red) transmitter photonic integrated circuit (PIC) (e.g., a silicon PIC) may be used for such spectrophotometric (or "spectroscopic") sensing. For example, a wearable device (e.g., a watch) or a portable device (e.g., a mobile telephone) may be equipped with a suitable transmitter and photodetector, and may conveniently perform such measurements without the need for the subject to visit a health care facility. The photonic integrated circuit may have an area of between about 10 $mm^2$ and about 100 $mm^2$, e.g., it may have an area of about 30 $mm^2$ or 70 $mm^2$. Integrated lasers in the photonic integrated circuit may be engineered to have accurate wavelengths and may cover a broad range of wavelengths, enabling the measurement of an absorbance spectrum suitable for detecting (or measuring the concentrations of) target biomarkers. However, if the transmitter PIC includes an array of lasers each having a fixed wavelength (or a wavelength tunable only over a small range), then relatively sparse sampling of the absorbance spectrum may be performed. In such an embodiment, the laser wavelength being transmitted at any time may be measured, to reduce sensing errors that may otherwise result from wavelength errors. Laser speckle may be another source of error. The return signal may include laser speckle patterns which may degrade the signal to noise ratio of the measurement of the intensity of the return signal. Various approaches (discussed in further detail below) may be taken to mitigate speckle.

FIG. 1A is a block diagram of a transmitter PIC, in some embodiments. An array of lasers 105 is configured to generate light at any one of a set (or "grid") of wavelengths. Each laser couples, when operating, laser light into a waveguide 110 connecting the laser to a multiplexer 115, which has a plurality of inputs (each connected to a waveguide connected to a respective one of the lasers 105) and an output, and which directs the light received at any of the inputs to a waveguide 110 connected to the output. The waveguides 110 may be single-mode waveguides. The output of the multiplexer 115 is connected to a coupler 120 having an input and two outputs. A first output of the coupler 120 (which may also be referred to as a "splitter") is connected to an output processing circuit 125 (which may be a homogenizer or a circuit for performing beam steering), an output of which forms the output 127 of the PIC (and from which the light may be transmitted into free space, through coupling optics or a window, and onto the skin of the subject). A second output of the coupler 120 is connected to a wavelength meter (or "wavemeter") 130 for measuring the wavelength of the transmitted light, and may also be connected to a photodetector 135 (which may be a photodiode, and which may be used for measuring the power of the light transmitted by the transmitter PIC). The light may be transmitted from the second output of the coupler to the wavelength meter 130 and to the photodetector 135 via one or more additional couplers (not explicitly illustrated in FIG. 1A). In some embodiments most of the optical power produced by the lasers is delivered to the output 127 of the transmitter PIC, and less than half (e.g., a fraction between 0.01% and 50%) is diverted to circuits (such as the wavemeter 130 and the photodetector 135) used to characterize the light. As used herein, a "wavemeter" is a component or system (e.g., a circuit) for measuring the wavelength of light. A wavemeter may include one or more wavemeters, as examples discussed below illustrate.

The multiplexer 115 may be a wavelength multiplexer, e.g., an arrayed waveguide grating (AWG) or an echelle grating (EG) (or any other suitable wavelength multiplexer, such as a Mach Zehnder interferometer (MZI) cascade). As used herein, a "multiplexer" (e.g., a wavelength multiplexer) is an optical element that combines optical signals (if present; some or all of the signals may be absent at some times) from a plurality of input waveguides into one or more output waveguides. A "wavelength multiplexer" is a multiplexer having the property that light having an ith wavelength, of a plurality of wavelengths, received at the jth input waveguide, is transmitted to a first output waveguide of the one or more output waveguides with a loss Lij, where for a first wavelength, a second wavelength, a first input waveguide and a second input waveguide,

L21>L11+L0,

L21>L22+L0,

L12>L11+L0, and

L12>L11+L0, where L0 is a wavelength-dependent loss between 1.0 dB and 200.0 dB.

A multiplexer may include a plurality of multiplexers (e.g., a plurality of wavelength multiplexers); for example, the outputs of an array of multiplexers may be combined, using couplers, to form a compound multiplexer. As another example, a compound multiplexer may include (i) a first stage including a plurality of multiplexers each multiplexing a respective subset of the inputs of the compound multiplexer into a respective intermediate waveguide, and (ii) a second stage, including an additional multiplexer multiplexing the intermediate waveguides into a single output waveguide.

Figure 1B:
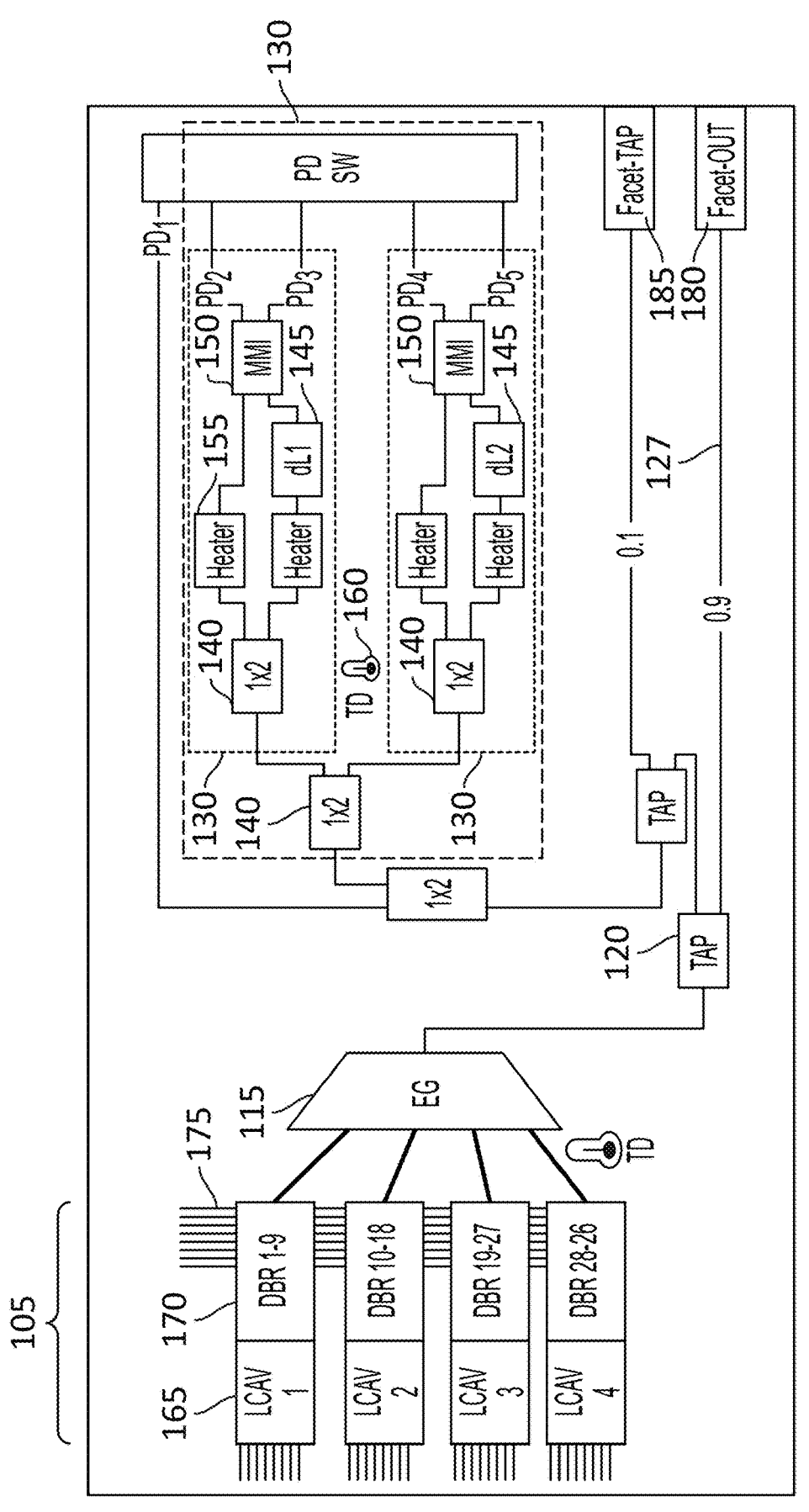
FIG. 1B is a block diagram of a photonic integrated circuit, according to an embodiment of the present disclosure.

FIG. 1B is a block diagram of a transmitter PIC, in some embodiments. Most (90%) of the light from the output of the multiplexer 115 (an echelle grating) is directed, by the coupler 120 (labeled "TAP"; as used herein a tap is a coupler with an unequal coupling ratio, the coupling ratio being less than 0.4) to the output 127 (where it is coupled into free space through an output facet 180 (discussed in further detail below)). As shown, the wavemeter 130 includes two unequal-arm Mach Zehnder interferometers, each of which operates as a wavemeter for measuring the wavelength of light at or near any one of a plurality of wavelengths at which the Mach Zehnder interferometer is near a quadrature point. A quadrature point of a Mach Zehnder interferometer may be an operating point at which, at one of the outputs of the Mach Zehnder interferometer, the contributions from the two arms of the Mach Zehnder interferometer are 90 degrees out of phase; at this operating point the rate of change of power at each of the outputs with respect to the wavelength of the received light may be greatest (and, accordingly, an error in the wavelength of a laser may result in the largest signal). In other embodiments the wavelength meter 130 may include or be an echelle grating, or a plurality of echelle gratings, suitably instrumented with photodetectors (e.g., photodiodes) connected to the output waveguide or waveguides of each echelle grating.

As such, in some embodiments, each wavelength of the laser wavelength grid is at or near the quadrature point of one of the wavemeter MZIs 130. The quadrature points of an MZI may be approximately evenly spaced in frequency, with two quadrature points (separated by half of the free spectral range (FSR) of the MZI) per FSR (the FSRs may also be approximately evenly spaced in frequency). The FSRs may therefore have a quadratic dependence on wavelength. Although it may be possible to sense wavelengths, using a single MZI, over the entire wavelength range of the transmitter PIC lasers (which may extend from about 1200 nm to about 2400 nm), in such an embodiment the spacing of the laser wavelength grid may increase significantly at the long wavelength end of the range, resulting in wavelength resolution, for the longer wavelengths, that may be too coarse for some sensing applications. As such, multiple MZIs, with different FSRs, may be included in the wavemeter 130, so that the wavelength spacing of the sensed wavelengths may be approximately the same at the short and long wavelength ends of the wavelength grid. FIG. 1B, for example, shows two MZIs (as mentioned above), each including a 1×2 coupler 140 configured as an input splitter, two arms, one including an additional delay 145 ("dL1" in the first MZI and "dL2" in the second MZI, each of which may be a section of waveguide), and a 2×2 multimode interference coupler (MMI) 150 configured as a combiner. One or both of the arms of each MZI may include a heater 155 configured to operate as a phase shifter (e.g., to compensate, using the thermo-optic effect, for an error in the differential phase delay caused by fabrication imperfections).

The MZI spectrum may shift with temperature because of the thermo-optic effect. The wavelength shift (e.g., of a quadrature point of the MZI) may be written as $$\Delta\lambda = \frac{\lambda}{n} \cdot \frac{dn}{dT}\Delta T \qquad (1)$$

where $\Delta\lambda$ is the wavelength shift, $\lambda$ is the wavelength, n is the index of refraction of silicon, and $$\frac{dn}{dT}$$

is the thermo-optic coefficient of silicon. To distinguish a wavelength error signal, from the wavemeter MZI, that is due to a PIC temperature change from one that is due to laser wavelength drift, the temperature of the wavemeter may be monitored using a temperature sensor 160 placed near the wavemeter MZIs. Such a sensor may be helpful in part because a uniform increase of (i) the distributed Bragg reflector grating 170 of the laser, (ii) the echelle grating, and (iii) the MZI wavemeter 130 may cause the laser wavelength to change without the wavelength change being detectable by the MZI wavemeter 130 (the index of refraction of which will have changed by substantially the same amount as those of the distributed Bragg reflector grating 170 of the laser and the echelle grating). The temperature sensor may be fabricated or selected to have an accuracy corresponding (based on Equation (1)) to the required wavelength accuracy of the wavemeter. The temperature sensor 160 may be a silicon diode temperature detector, or "temperature diode" (TD), which may be integrated into the Si PIC process flow. In some embodiments, a resistor temperature detector (RTD), which may also be integrated into the PIC process, may be used instead of, or in addition to, a silicon diode temperature detector. Materials such as platinum or nickel may be used for an RTD. In some embodiments, the temperature sensor 160 is an external thermistor bonded to the PIC.

Each of the lasers 105 may include a semiconductor optical amplifier (SOA) 165, e.g., a reflective SOA (RSOA), which may be formed in a waveguide on a III-V semiconductor chip. The III-V semiconductor chip may be in (e.g., bonded into) a cavity in the transmitter PIC. The transmitter PIC may be a silicon photonic integrated circuit with silicon waveguides 110 (e.g., single-mode waveguides) one of which may (i) include a distributed Bragg reflector (DBR) grating 170 for setting the operating wavelength of the laser 105, and (ii) be butt-coupled to the waveguide of the semiconductor optical amplifier 165. In operation, one laser 105 at a time may be turned on (e.g., for 1 ms, of which the initial 0.2 ms may be used to allow the laser to stabilize, and the remaining 0.8 ms may be used for data acquisition), and that laser's wavelength may be measured using the corresponding wavemeter MZI 130. In some embodiments, intervals (e.g., 0.2 ms long intervals) during which all of the lasers are turned off may be used to measure dark current. These dark current measurements may be frequent (e.g., every ms) or infrequent (e.g., once every few minutes).

The array of lasers 105 may include about 100 lasers 105 (e.g., it may include between 35 and 300 lasers 105). The lasers 105 may be grouped into bands, within which the spacing of the laser frequencies may be substantially uniform. Gaps may be present between some adjacent pairs of bands, in part because water absorption peaks at 1440 nm and 1900 nm may limit the signal to noise ratio achievable near those wavelengths. In some embodiments, the wavelength grid includes one or more of three bands, the first band extending from within 10% of 1350 nm to within 10% of 1410 nm, the second band extending from within 10% of 1550 nm to within 10% of 1770 nm, and the third band extending from within 10% of 2060 nm to within 10% of 2330 nm. The wavelength separation between lasers that are at adjacent wavelengths within any of the three bands may be between 4 nm and 10 nm (e.g., between 5 nm and 8 nm).

Each distributed Bragg reflector grating may be equipped with a heater, which may be used (i) to tune the laser wavelength (via the therm o-optic effect), or (ii) to stabilize the wavelength (by maintaining the temperature at a fixed temperature greater than the highest expected ambient temperature), or (iii) to align the laser wavelength to the wavelength grid, e.g., if there is a misalignment due to fabrication process variability. FIG. 1B shows conductors 175 that may carry a respective current to each of the heaters.

Light may be transmitted from the transmitter PIC at an output facet 180 (the embodiment of FIG. 1B lacks the output processing circuit 125). One or more test input facets 185 (one, in the embodiment of FIG. 1B, labelled "FACET-TAP"; in some embodiments there are several, e.g., two, labeled "FACET-TAP-A" and "FACET-TAP-B" in the drawings), which may be waveguide facets at one or more edges of the transmitter PIC, may be used to calibrate, and test the operation of, the wavemeters 130.

Figure 2A:
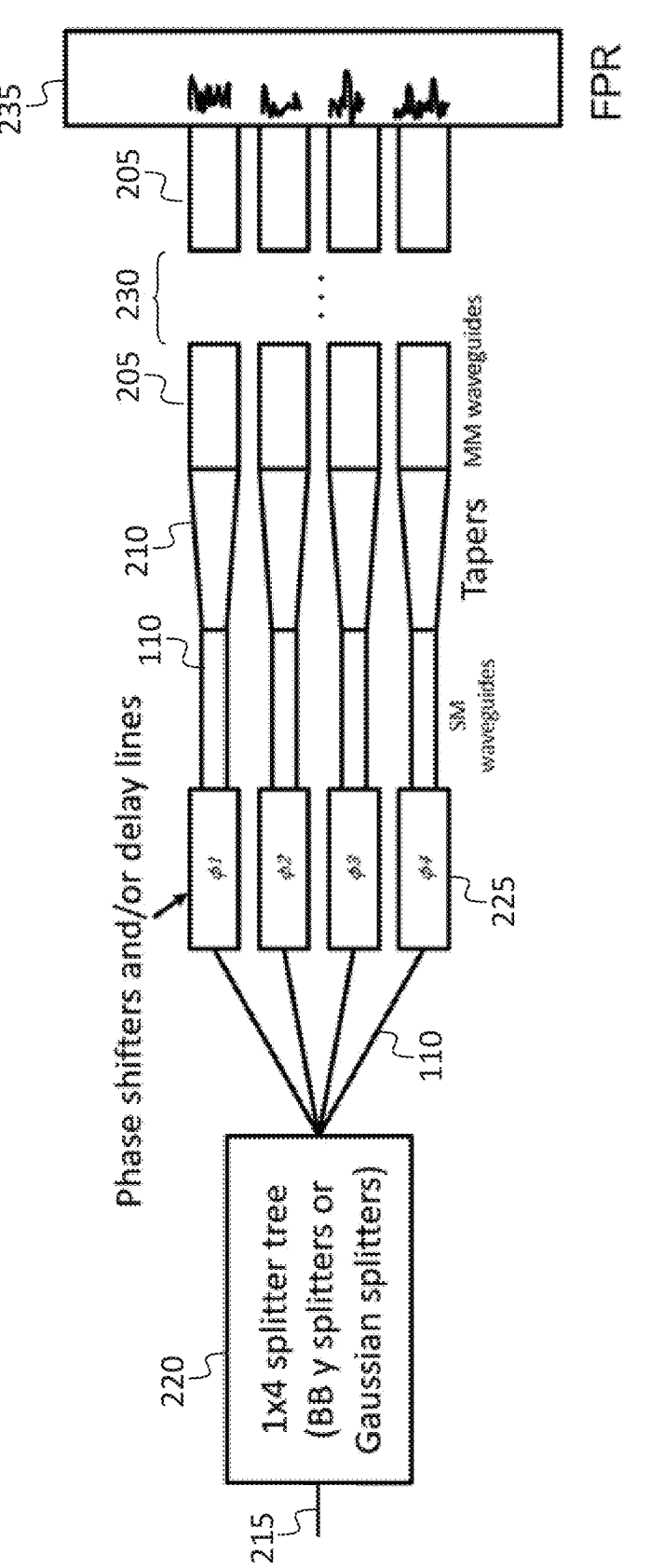
FIG. 2A is a schematic drawing of a portion of a photonic integrated circuit, according to an embodiment of the present disclosure.

In some embodiments, the transmitter PIC includes an on-chip homogenizer, and example of which is illustrated in FIG. 2A. The output from the transmitter PIC may be an output facet of a free propagation region (FPR) 235 fed by one or more multi-mode (MM) waveguides 205, and the effect of the homogenizer may be to cause the optical power propagating in each multi-mode waveguide 205 to be more uniformly distributed among the spatial modes than when it is first coupled into the multi-mode waveguide 205 from a single mode waveguide 110 (e.g., through a taper 210, as shown). The homogenizer may assist with speckle mitigation. As shown in FIG. 2A, the light received at the input 215 of the homogenizer may be split into a plurality of paths (e.g., four paths as shown), for example by a 1×4 splitter that may be constructed as a 1×4 splitter tree 220 including broadband Y-splitters or Gaussian splitters, and fed into a plurality of parallel paths, each of which may include, as shown, a phase shifter 225 (which may be an active (e.g., thermally controlled) phase shifter), a single mode waveguide 110, a taper 210, and a multimode waveguide 205. Within each of the multimode waveguides 205 (in a section 230 identified by the ellipsis in FIG. 2A) may be an arc or spiral to promote mode mixing within the multimode waveguide 205. Each of the multi-mode waveguides 205 may be connected to the free propagation region 235 which may be at an edge of the transmitter PIC and which may provide an interface for coupling the output light into free space.

Figures 2B, 2C, 2D:
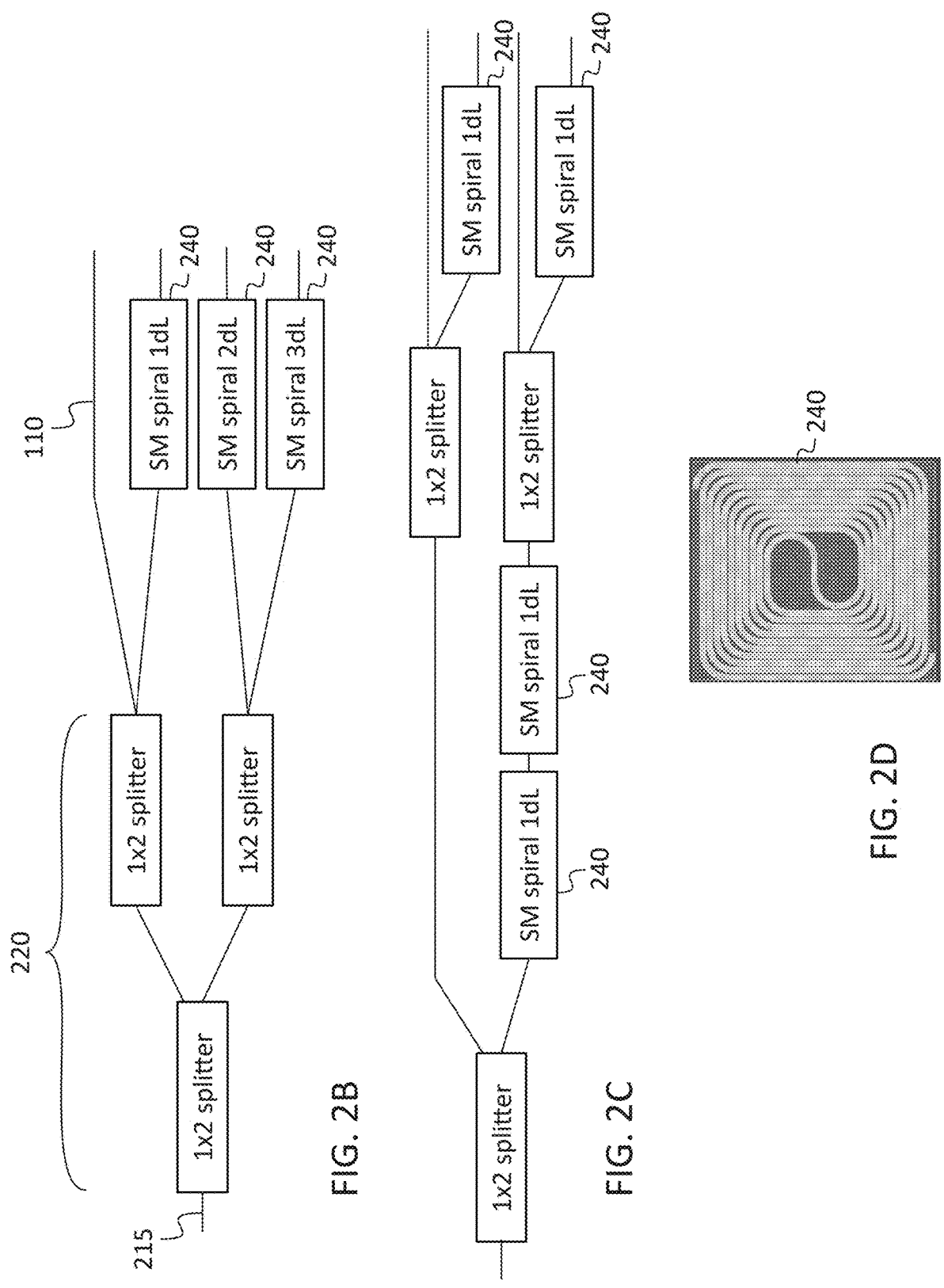
FIG. 2B is a schematic drawing of a portion of a photonic integrated circuit, according to an embodiment of the present disclosure.
FIG. 2C is a schematic drawing of a portion of a photonic integrated circuit, according to an embodiment of the present disclosure.
FIG. 2D is a top view of a spiral waveguide, according to an embodiment of the present disclosure.

Referring to FIG. 2B, in some embodiments, phase shifters may be used to steer the free space beam by causing the waveguide ends to operate as a 4-channel optical phased array (OPA). The phase shifters may be active phase shifters (e.g., thermally controlled phase shifters, each including a section of waveguide and a heater, for heating the waveguide, in response to an electrical drive signal). In some embodiments, the phase shifters 225 are passive phase shifters, which may be constructed as different lengths of waveguide 110 the phase delay of which may be adjusted by adjusting the laser wavelength. For example, the drive current of the currently active laser, or the heater current applied to the heater of the distributed Bragg reflector grating 170, may be adjusted, causing the wavelength of the laser, and the phase delay of each phase shifter 225 to change. If the phase changes in the phase shifters 225 are different, this mechanism may be used to steer the output beam (in the free propagation region 235, and in free space on the other side of the free propagation region 235). Changing the direction of the beam and the total optical pathlength beneath the surface of the skin of the subject may result in different speckle patterns at the receiver photodiodes, which, when averaged (either by the detection circuit, or by subsequent processing), may diminish the effects of speckle. In some embodiments the free space beam may reflect from a deformable reflector 420 (FIG. 4) before illuminating the skin of the subject. In such an embodiment the deformable reflector 420 may apply a spatially varying phase modulation to the light reflected from it, and the passive optical phased array may steer the beam, e.g., back and forth across the deformable reflector, for speckle mitigation. As in the embodiment of FIG. 2A, the output from the transmitter PIC may be an output facet of a free propagation region (like that of FIG. 2A, and not shown in FIGS. 2B and 2C), fed by the waveguides on the right-hand side of FIG. 2B (or FIG. 2C). The presence of the free propagation region may facilitate the fabrication of the transmitter PIC, by avoiding certain fabrication challenges that may be present when an array of waveguides on a small pitch is coupled to free space at the edge of a chip.

FIGS. 2B and 2C show passive optical phased arrays according to two respective embodiments. In the embodiment of FIG. 2B, light at the input 215 is split into four paths by a two-stage splitter tree 220, and each of the four paths includes a different delay. The top-most path includes a first delay (e.g., the delay of a section of waveguide), the second path from the top includes the first delay and one increment of additional delay (1 dL), the third path from the top includes the first delay and two increments of additional delay (2 dL), and the fourth path from the top includes the first delay and three increments of additional delay (3 dL). In each case the additional delay may be provided by a single mode (SM) spiral waveguide 240, e.g., a waveguide having a layout as illustrated in FIG. 2D (which, in the embodiment of FIG. 2D, may have outer dimensions of between 0.5 and 2.0 mm by between 0.5 and 2.0 mm, e.g., 1 mm×1 mm or 2 mm×2 mm). In the embodiment of FIG. 2C, the nominal delay differences at the outputs are the same as in FIG. 2B, but two increments of delay, of the delays in the third and fourth paths, are provided by one or more shared delay elements (e.g., a cascade of two spiral waveguides 240 (i.e., two spiral waveguides 240, connected in cascade), within the 1×4 splitter tree 220 as shown). In the embodiment of FIG. 2C, fabrication imperfections may have a reduced effect on the uniformity of the phase differences at the outputs. For example, an imperfection in a shared spiral waveguide 240 in the 1×4 splitter tree 220 may have no effect on the phase difference between the third and fourth paths. Moreover, if, as shown in FIG. 2C, all of the additional delays are provided by the same design of spiral waveguide 240, producing one increment of delay, then fabrication imperfections may produce the same change in delay in each of them. The improved uniformity may improve the beam quality of the beam launched by the optical phased array.

In some embodiments, the delay increment is selected such that the desired total change in beam direction (e.g., corresponding to the field of view (FOV) of the beam) corresponds to a wavelength change that is less than (e.g., is less than half of, or is a value between 0.1 and 0.3 times) the wavelength separation between adjacent longitudinal (cavity) modes of the laser, to reduce the risk that the wavelength tuning used to perform beam steering will cause the laser to exhibit a mode hop. For example, if the wavelength change $\Delta\lambda$ corresponding to the desired change in beam direction is half of the wavelength separation between adjacent longitudinal (cavity) modes of the laser, then the system may perform a test sweep, starting at an initial wavelength $\lambda_0$ and increasing the wavelength continuously to $\lambda_0+\Delta\lambda$, while monitoring (e.g., monitoring the output of the wavemeter 130 corresponding to the laser, or using an external instrument) for indications of a mode hop. If a mode hop is detected, the system may define a new starting wavelength, $\lambda_1=\lambda_0+\Delta\lambda$, and, in operation, perform beam steering by adjusting the wavelength between $\lambda_1$ and $\lambda_1+\Delta\lambda$.

Figure 3A:
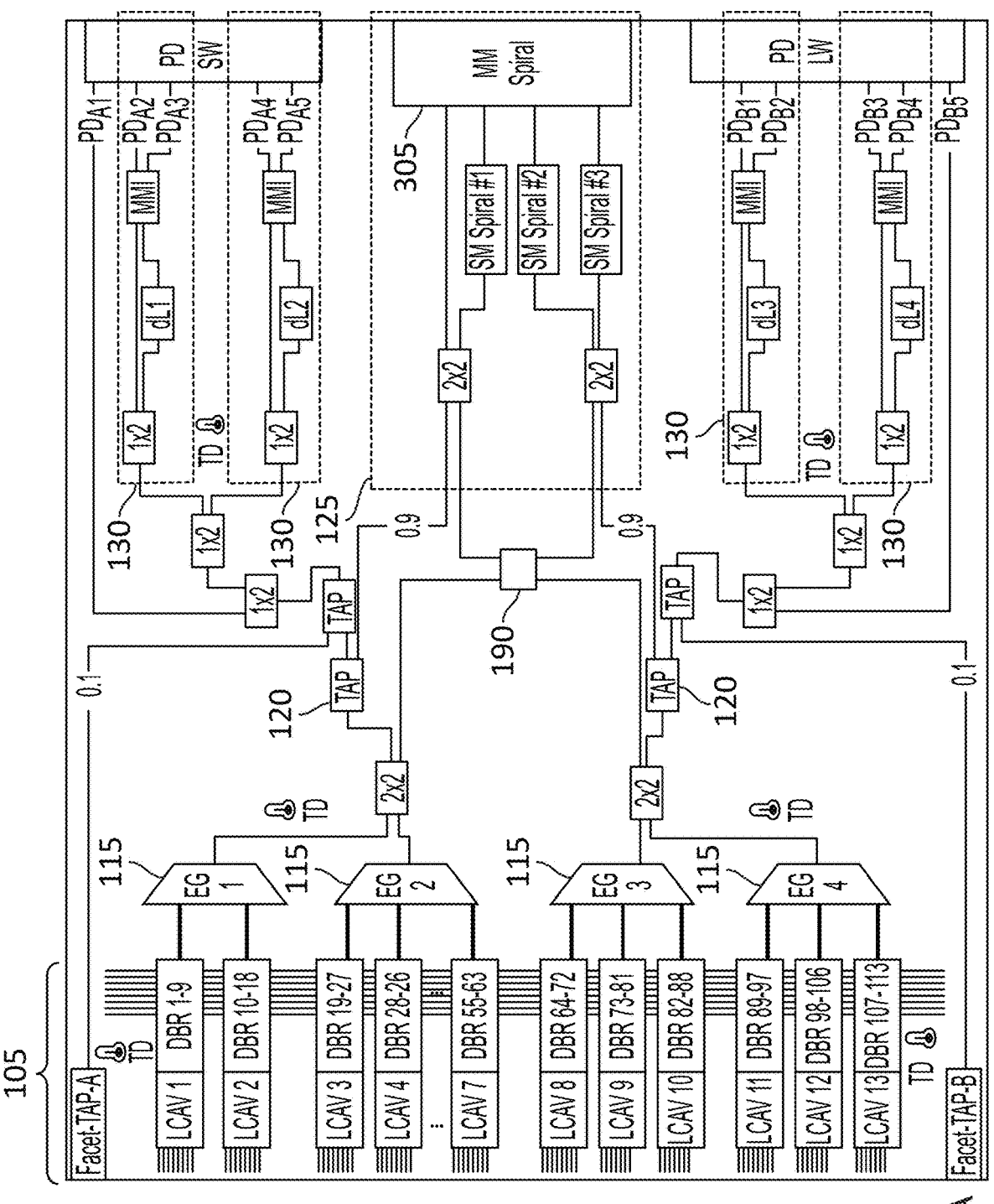
FIG. 3A is a block diagram of a photonic integrated circuit, according to an embodiment of the present disclosure.

FIG. 3A shows an example of a silicon transmitter PIC with multiple III-V dies integrated into laser cavities in the transmitter PIC, which may cover a wavelength range from 1300 nm to 2400 nm in steps (increments) of about 7 nm (e.g., in increments of between 2 nm and 20 nm). Although FIG. 3A is a block diagram, in some embodiments the location of each component on the transmitter PIC is substantially as shown. As mentioned above, the laser wavelength grid may be divided into four bands. Within each band the laser frequency spacing is substantially fixed, and substantially equal to an integer multiple of one-half of the FSR of a respective one of the four wavemeter MZIs 130. Within each band, the lasers are multiplexed into a single waveguide 110 for the band by a respective multiplexer 115 (e.g., an echelle grating, as illustrated). The architecture uses four echelle gratings, one for each wavelength band, and passive 2×2 combiners to multiplex all the wavelengths into four output waveguides.

From each multiplexer, a fraction (e.g., about 1%) of the light is sent to two wavemeter MZIs 130, and the wavemeter MZI 130 corresponding to the wavelength band containing the active laser may be used to measure the wavelength. The two outputs of each of the wavemeter MZIs 130 are connected to a pair of photodetectors (PD_A2-A5 and PD B1-B4 in FIG. 3A). The photocurrents from the wavemeter photodetectors are used to measure the laser wavelength in real time, during operation. Two on-chip power monitoring photodetectors, labeled PD_A1 and PD_B1, may be used for measuring the total power produced by the currently active laser, and for normalizing the wavemeter photocurrents and the photocurrents of the receiver photodetectors.

Most of the optical power of the currently active laser is sent to a multimode spiral homogenizer 305 having four input channels. The multimode spiral 305 may be used for generating de-correlated intensity patterns at the output of the multimode spiral, for speckle suppression. The four input channels with different delay line lengths may modulate the wavefront direction at the input of the multimode spiral when the wavelength of the currently active laser is adjusted (by adjusting the laser current or the temperature of the distributed Bragg reflector grating 170, as mentioned above). A waveguide crossing 190 is used to allow one waveguide to cross over (or under) another, allowing, e.g., light from the first and second multiplexers 115 (EG 1 and EG 2) to reach the lower two waveguides feeding the multimode spiral 305.

Temperature detectors may be placed near the laser cavities, near the multiplexers 115, and (as mentioned above) near the wavemeters 130 to monitor the temperature. Diode temperature detectors (DTDs) (as illustrated), thermistors, or RTDs may be used for this purpose.

Figure 3B:
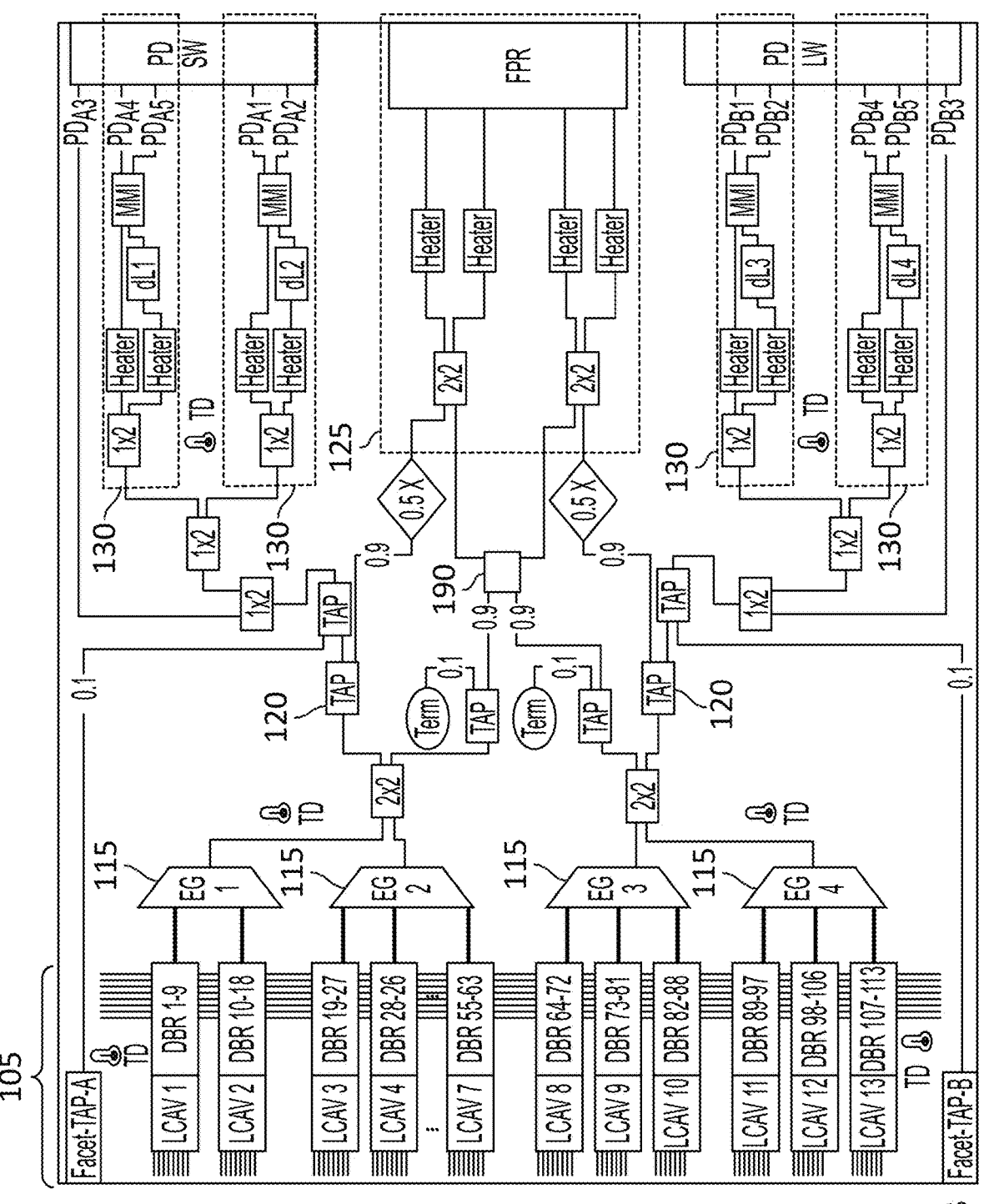
FIG. 3B is a block diagram of a photonic integrated circuit, according to an embodiment of the present disclosure.

FIG. 3B shows another example of a silicon transmitter PIC, which differs from that of FIG. 3A in that the transmitter PIC of FIG. 3B has heaters in the wavemeter MZIs 130. Although FIG. 3B is a block diagram, in some embodiments the location of each component on the transmitter PIC is substantially as shown. The heaters (like other heaters described herein) may be doped silicon heaters or metal heaters on waveguides, which are used to change the optical phase through the thermo-optic effect. The heaters may be used to align the MZI quadrature points to the laser wavelength grid in case there is an unacceptable phase error in any of the MZI wavemeters 130 due to fabrication process variability. In the embodiment of FIG. 3B, the output processing circuit 125 includes a four-channel optical phased array with a heater on each arm for speckle mitigation. The output beam may be dynamically steered, by adjusting the relative phases in the four arms (using the four heaters). As mentioned above, changing the direction of the beam and the total optical pathlength within skin may result in different speckle patterns at the receiver photodetectors, which, when averaged together, may reduce speckle noise.

In the embodiments of FIGS. 3A and 3B, there may be a one-to-one correspondence between multiplexers 115 and wavemeters 130, e.g., each multiplexer 115 corresponds to a respective wavemeter 130, which is configured to measure each of the wavelengths received by the multiplexer. In other embodiments, the wavelengths multiplexed by a multiplexer 115 may be detected by different wavemeters 130, or a wavemeter 130 may detect wavelengths multiplexed by different multiplexers 115. Electrical connections may be made to the laser amplifiers (LCAV) using wire bonds. In the embodiments of FIGS. 3A and 3B all of the wire bonds may be made along one edge of the photonic integrated circuit, facilitating the wire bonding process.

Figure 3C:
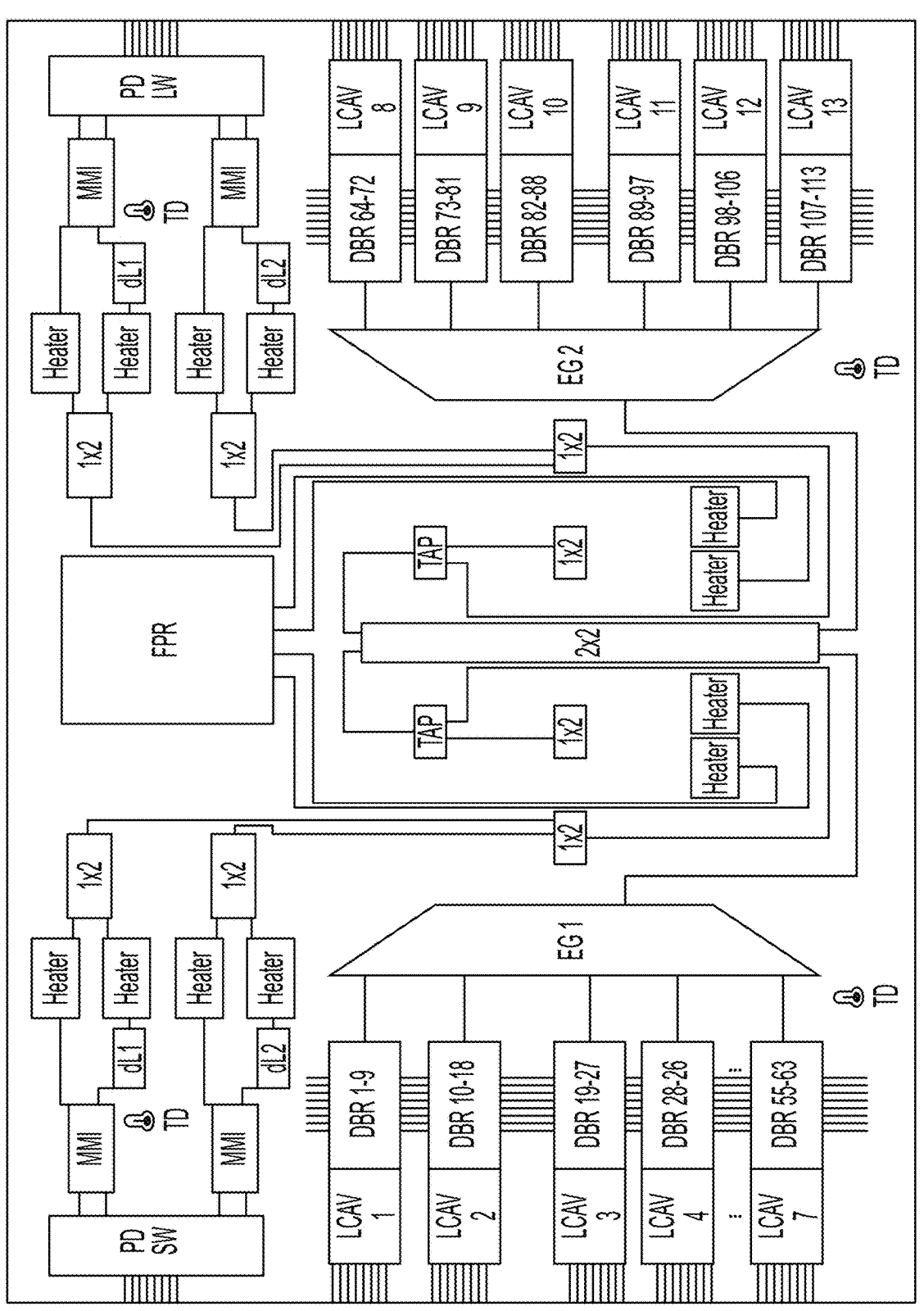
FIG. 3C is a block diagram of a photonic integrated circuit, according to an embodiment of the present disclosure.
Figure 3D:
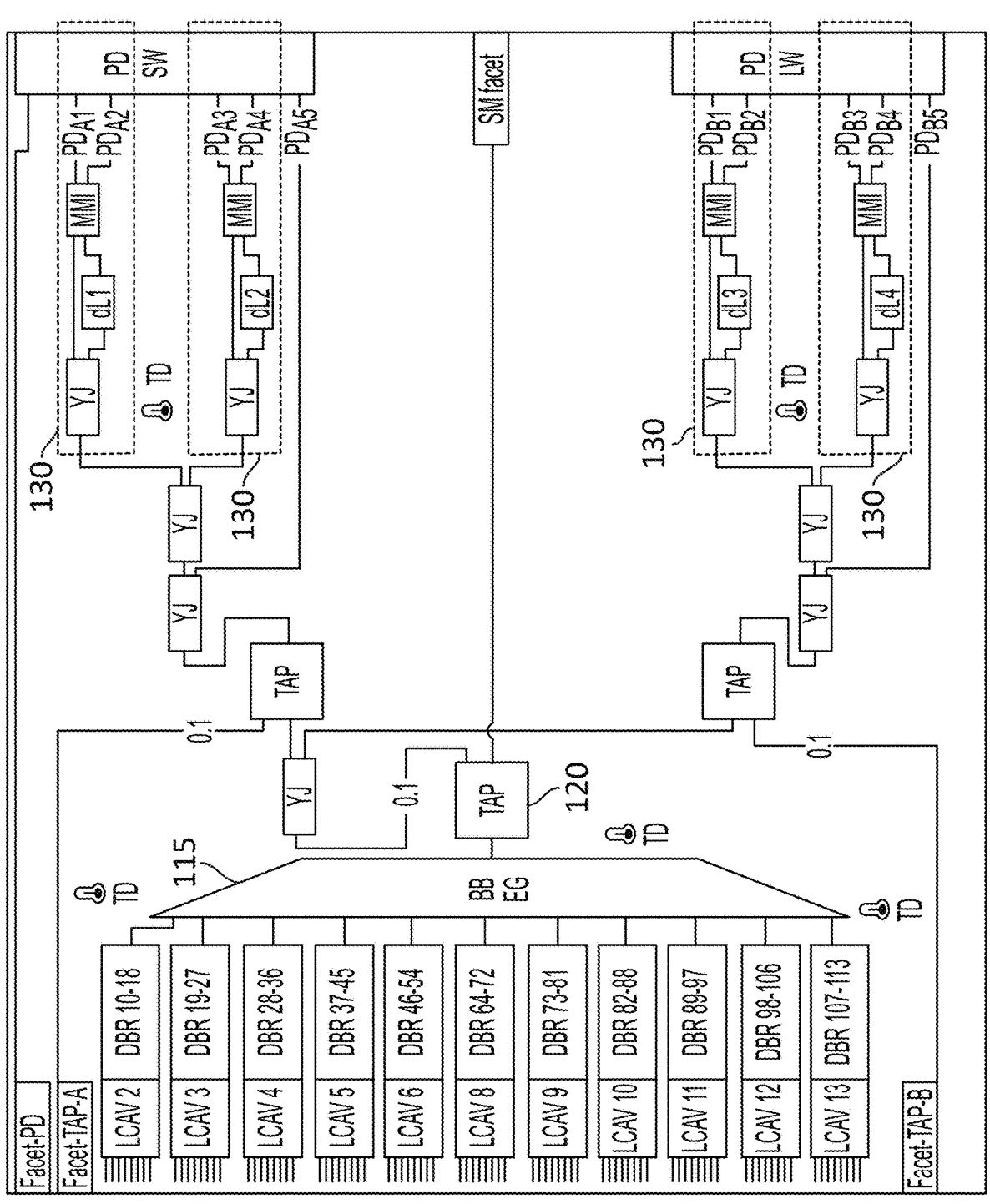
FIG. 3D is a block diagram of a photonic integrated circuit, according to an embodiment of the present disclosure.
Figure 3E:
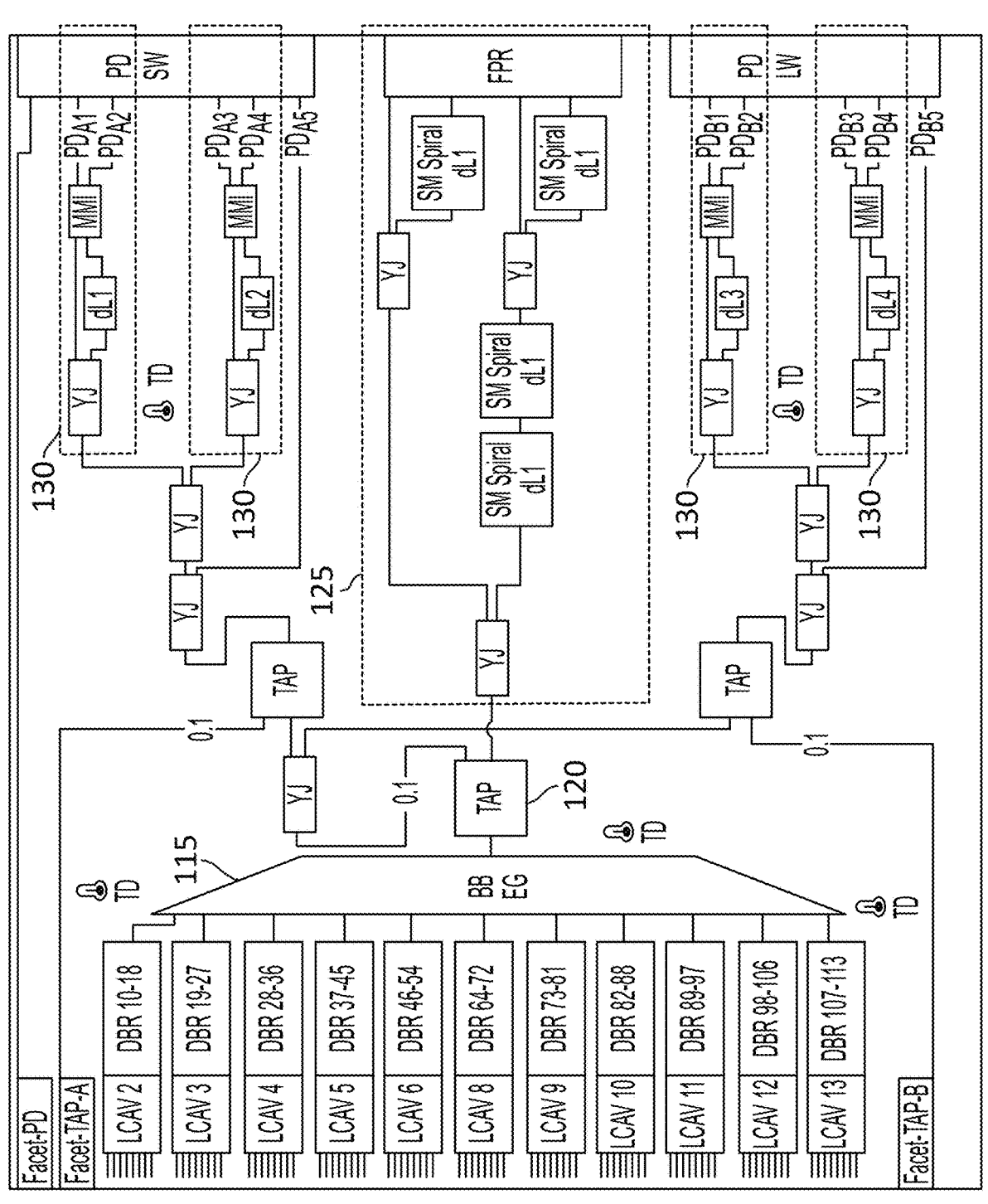
FIG. 3E is a block diagram of a photonic integrated circuit, according to an embodiment of the present disclosure.

FIG. 3C is a block diagram of a transmitter PIC, in some embodiments. Although FIG. 3C is a block diagram, in some embodiments the location of each component on the transmitter PIC is substantially as shown. FIGS. 3D and 3E differ from the embodiments of FIGS. 3A-3C primarily in that in FIG. 3D, a single echelle grating is used to multiplex together all of the lasers. FIG. 3E differs from FIG. 3D in that FIG. 3E includes, as the output processing circuit 125, a passive optical phased array according to the embodiment of FIG. 2C, whereas FIG. 3D lacks an output processing circuit 125. In FIGS. 3D and 3E various splitters are implemented as broadband Y junctions (each labeled "YJ"). The embodiment of FIG. 3C avoids the need for a waveguide crossing and it allows good phase balance between all four input waveguides before the free propagation region (FPR).

For performing spectroscopic (e.g., spectrophotometric) measurements, the transmitter PIC may be packaged with an application-specific integrated circuit (ASIC) driver. The ASIC driver may control the operation of active devices including lasers, monitor photodiodes, transimpedance amplifiers, heaters and temperature sensors. The grating heater and the optical phased array heaters may be modulated during data acquisition, for speckle mitigation. The photocurrents from the wavemeter photodiodes and the power monitor photodiodes, and the temperature sensor voltage may be read out through analog to digital conversion during this time. The order in which the lasers are turned on may be chosen so as to minimize thermal crosstalk between the lasers. For example, each III-V chip may include an array of (e.g., between 5 and 15) semiconductor optical amplifiers 165, that may be thermally coupled as a result. In some embodiments, after a first laser on a first III-V chip has been used, a laser on each of the other III-V chips is used before another laser on the first III-V chip is used, so that the temperature of the first III-V chip has as much time as possible to stabilize between operating intervals.

Figure 4:
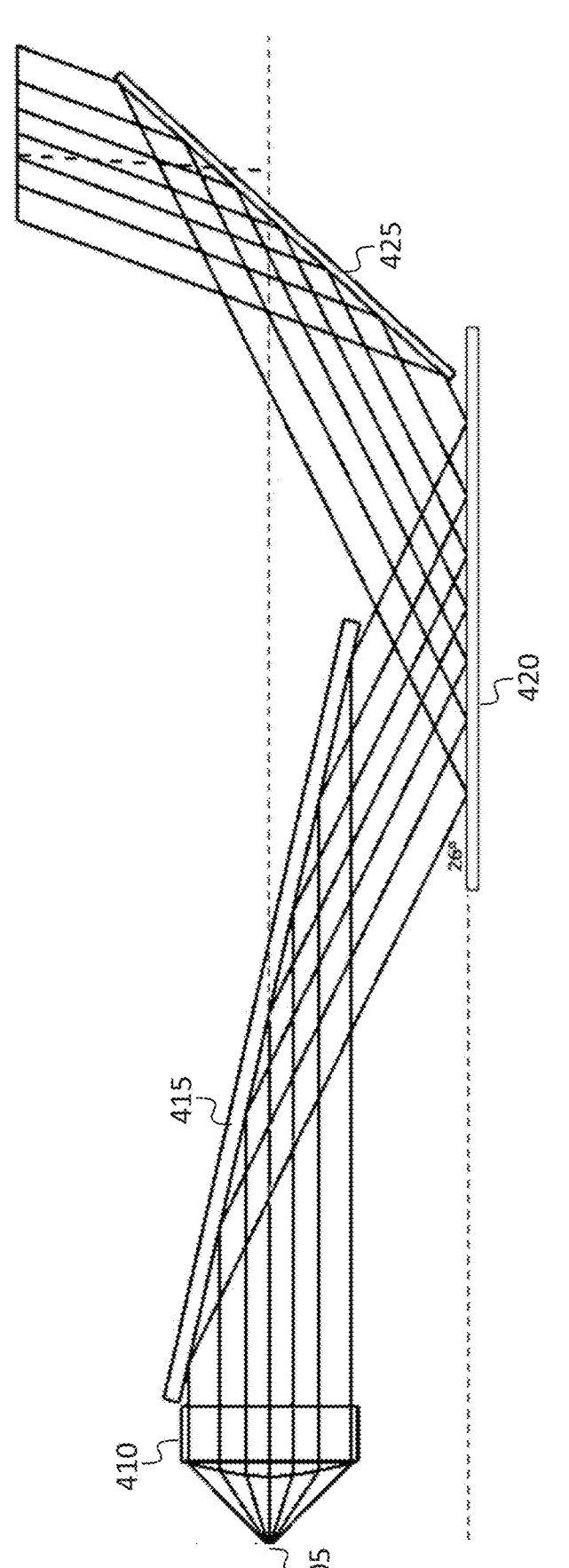
FIG. 4 is a side view of an optical layout, according to an embodiment of the present disclosure.

FIG. 4 is a side view of an optical layout for directing the free-space beam produced at the output interface 405 (e.g., the output facet of the free propagation region 235) of the transmitter PIC. The beam is collimated by a lens 410, redirected by a first folding mirror 415 onto a deformable reflector 420, reflected by the deformable reflector 420, and redirected by a second folding mirror 425.

As used herein, a "circuit" is either an electrical circuit, in which electrical signals propagate on conductors, or an optical circuit, in which optical signals propagate in waveguides, or a combination of both. As used herein, a "splitter" is a coupler with one input and N outputs; as such (e.g., as in the example of FIG. 2A), a splitter may include a plurality of splitters.

As used herein, "a portion of" something means "at least some of" the thing, and as such may mean less than all of, or all of, the thing. As such, "a portion of" a thing includes the entire thing as a special case, i.e., the entire thing is an example of a portion of the thing. As used herein, when a second quantity is "within Y" of a first quantity X, it means that the second quantity is at least X-Y and the second quantity is at most X+Y. As used herein, when a second number is "within Y%" of a first number, it means that the second number is at least $(1-Y/100)$ times the first number and the second number is at most $(1+Y/100)$ times the first number. As used herein, the word "or" is inclusive, so that, for example, "A or B" means any one of (i) A, (ii) B, and (iii) A and B.

The terminology used herein is for the purpose of describing particular embodiments only and is not intended to be limiting of the inventive concept. As used herein, the terms "substantially," "about," and similar terms are used as terms of approximation and not as terms of degree, and are intended to account for the inherent deviations in measured or calculated values that would be recognized by those of ordinary skill in the art.

It will be understood that when an element is referred to as being "immediately connected" or "immediately coupled" to another element, there are no intervening elements present. As used herein, "connected" means connected by a signal path (e.g., a conductor or a waveguide) that may contain arbitrary intervening elements, including intervening elements the presence of which qualitatively changes the behavior of the circuit. As used herein, "directly connected" means (i) "immediately connected" or (ii) connected with intervening elements, the intervening elements being ones (e.g., low-value resistors or inductors, short sections of transmission line, or short sections of waveguide) that do not qualitatively affect the behavior of the circuit.

Any numerical range recited herein is intended to include all sub-ranges of the same numerical precision subsumed within the recited range. For example, a range of "1.0 to 10.0" or "between 1.0 and 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Similarly, a range described as "within 35% of 10" is intended to include all subranges between (and including) the recited minimum value of 6.5 (i.e., $(1-35/100)$ times 10) and the recited maximum value of 13.5 (i.e., $(1+35/100)$ times 10), that is, having a minimum value equal to or greater than 6.5 and a maximum value equal to or less than 13.5, such as, for example, 7.4 to 10.6. Any maximum numerical limitation recited herein is intended to include all lower numerical limitations subsumed therein and any minimum numerical limitation recited in this specification is intended to include all higher numerical limitations subsumed therein.

Although exemplary embodiments of an optical transmitter have been specifically described and illustrated herein, many modifications and variations will be apparent to those skilled in the art. Accordingly, it is to be understood that an optical transmitter constructed according to principles of this disclosure may be embodied other than as specifically described herein. The invention is also defined in the following claims, and equivalents thereof.

What is claimed is:

1. A system, comprising:
a first array of lasers;
a first wavelength multiplexer, connected to the first array of lasers;
a first coupler, connected to the first wavelength multiplexer;
a first wavelength meter, connected to a first output of the first coupler; and
a first splitter having an input, a first output and a second output, wherein a first output of the first coupler is connected to the input of the first splitter,
wherein:
the first output of the first splitter is connected through a first optical path to a free propagation region; and
the second output of the first splitter is connected through a second optical path to the free propagation region.

2. The system of claim 1, wherein the first coupler is configured to deliver at least 70% of optical power received at a first input of the first coupler to the first output of the first coupler.

3. The system of claim 1, wherein the first coupler further has:
a first input; and
a second input connected to a test input facet.

4. The system of claim 1, wherein a length of the second optical path is at least 10% greater than a length of the first optical path.

5. The system of claim 4, wherein:
the first optical path and the second optical path are part of a passive optical phased array configured to steer an output beam through an angle corresponding to a wavelength change; and the wavelength change is less than a longitudinal mode spacing of a laser of the first array of lasers.

6. The system of claim 4, wherein the second optical path comprises a spiral waveguide.

7. The system of claim 4, wherein the first optical path comprises a multimode waveguide and the second optical path comprises a multimode waveguide.

8. The system of claim 1, wherein the first optical path comprises a heater.

9. The system of claim 1, comprising an optical phased array comprising the first optical path and the second optical path, and further comprising a deformable reflector, the optical phased array being configured to steer a free-space beam across the deformable reflector.

10. The system of claim 1, further comprising:
a first cascade of one or more spiral waveguides connected to the second output of the first splitter;
a second splitter having an input, a first output, and a second output, the input of the second splitter being connected to the first output of the first splitter;
a third splitter having an input, a first output, and a second output, the input of the third splitter being connected to the first cascade of one or more spiral waveguides;
a second cascade of one or more spiral waveguides connected to the second output of the second splitter; and
a third cascade of one or more spiral waveguides connected to the second output of the third splitter.

11. The system of claim 1, wherein the first array of lasers comprises 50 lasers.

12. The system of claim 1, wherein a wavelength separation of two lasers of the first array of lasers is between 3 nm and 15 nm.

13. The system of claim 1, further comprising a temperature sensor configured to measure a temperature of the first wavelength meter.

14. The system of claim 13, wherein the temperature sensor is a diode temperature detector.

15. The system of claim 1, further comprising a photodiode configured to receive a portion of light at a second output of the first coupler and to measure an output power of a currently operating laser.

16. The system of claim 1, wherein the first wavelength multiplexer, the first coupler, and the first wavelength meter are integrated onto a silicon photonic integrated circuit.

17. A system, comprising:
a first array of lasers;
a first wavelength multiplexer, connected to the first array of lasers;
a first coupler, connected to the first wavelength multiplexer;
a first wavelength meter, connected to a first output of the first coupler;
a second array of lasers;
a second wavelength multiplexer; and
a second wavelength meter,
the second wavelength multiplexer having:
a plurality of inputs each connected to a respective one of the lasers of the second array of lasers, and
an output,
the output of the second wavelength multiplexer being connected to the second wavelength meter,
wherein:
the first wavelength meter is a Mach Zehnder interferometer wavelength meter,
the second wavelength meter is a Mach Zehnder interferometer wavelength meter,
frequencies of the lasers of the first array of lasers are uniformly spaced to within 20%,
frequencies of the lasers of the second array of lasers are uniformly spaced to within 20%,
an average frequency separation of the lasers of the first array of lasers is greater than an average frequency separation of the lasers of the second array of lasers by at least 30%,
N/2 times a free spectral range of the first wavelength meter is within 10% of the average frequency separation of the lasers of the first array of lasers,
M/2 times a free spectral range of the second wavelength meter is within 10% of the average frequency separation of the lasers of the second array of lasers, and
N and M are integers.

* * * * *